United States Patent [19]
Djavit

[11] Patent Number: 6,024,257
[45] Date of Patent: Feb. 15, 2000

[54] PINCH VALVE FOR A DRAINAGE BAG AND A METHOD OF ASSEMBLY

[75] Inventor: Nuri Djavit, London, United Kingdom

[73] Assignee: Bristol-Myers Squibb Company, New York, N.Y.

[21] Appl. No.: 09/024,824

[22] Filed: Feb. 17, 1998

[51] Int. Cl.$^7$ .................................................. B65D 37/00
[52] U.S. Cl. ................................ 222/212; 251/4; 251/10
[58] Field of Search ................................ 222/212, 556; 251/4, 10

[56] References Cited

U.S. PATENT DOCUMENTS

| 4,736,925 | 4/1988 | Kamstrup-larsen et al. ............. 251/10 |
| 5,072,855 | 12/1991 | Herzig ..................................... 222/212 |

Primary Examiner—Philippe Derakshani
Attorney, Agent, or Firm—Stuart E. Krieger

[57] ABSTRACT

A drainage bag (for example a urine collection bag) (10) includes a flexible outlet tube (16) and a pinch valve (18) for selectively pinching the tube closed. The pinch valve includes a pivotal valve member (22) on a first side of the bag, and a support member (20) on an opposite side of the bag. The valve member is pivotally supported on the first side by at least one projection (26) on the support member which projects through an aperture (24) in a web of the bag. During assembly, the support member (20) is firstly fitted to the bag with the projection (26) projecting through the aperture (34), and the valve member (22) is then fitted to the projection (26). In an alternative form, the support has two hook-shaped projections on either side of the outlet tube (16) to which a modified valve member is clipped.

24 Claims, 6 Drawing Sheets

PINCH VALVE FOR A DRAINAGE BAG AND A METHOD OF ASSEMBLY

This invention relates to a pinch valve for use with a drainage bag, and also to a method of assembling a valve and a drainage bag.

Such valves and bags are mainly used with discharge collection systems for medical or hygienic purposes, for example, urine collection bags for incontinence appliances, or ostomy bags for ostomy appliances. The valve enables the user to drain the contents of the bag, for example into a WC, and then to re-seal the bag so that it can be used again.

Typically, the bag will consist of two sheets of thin plastics material welded together around the periphery, and having an inlet tube or aperture towards an upper end, and an outlet tube at the lower end. An example of such a bag fitted with a pinch valve is known from U.S. Pat. No. 4,736,925. In that design, the valve consists of a U-shaped channel member at one end of which is mounted a pivotal clamp member. The clamp member is assembled to the channel member prior to fitting to the pouch and, thereafter, the assembled valve is fitted by sliding the channel member over the lower end of the outlet tube. The channel member has slots in each side wall so that the channel member can overlap the peripheral flange formed by the welded edges of the bag.

With such a design of valve, there is no positive retention of the valve relative to the bag. Particularly when the clamp member is lifted (to un-pinch the outlet tube), the valve is held in position only loosely by the engagement of the peripheral flange in the slots of the channel walls. If the slots are made very narrow, to provide better frictional grip with the bag, then it may be difficult to fit the valve initially to the bag. On the other hand, if the slots are relatively wide to facilitate the initial fitting, then the slots will not generate good frictional engagement to retain the valve in position.

The present invention has been devised bearing in mind the problems of the prior art.

In contrast to the prior art, the present invention provides, in a first aspect, a drainage bag including a flexible outlet tube and a pinch valve for selectively pinching the tube closed, the pinch valve including a pivotal valve member on a first side of the bag and a support member on an opposite side of the bag, wherein the valve member has a handle projection and is pivotally supported on the first side of the bag by at least one projection on the support member which projects through an aperture in a web of the bag to the first side, the valve member being movable by its handle about a pivot axis which is generally transverse to the direction in which the tube is pinched.

With such an arrangement, the one or more support member projections passing through the web of the bag can provide positive location and retention of the valve assembly on the bag, even when the valve is in an open position.

The projection may, for example, comprise a transverse bore for receiving a pivot pin portion of the valve member, or it may, for example, comprise a hook-shaped lug for receiving such a pivot pin portion.

In a first preferred embodiment, the support member has a single projection in the form of a post. The valve member has an integral pivot pin which can be received in a transverse bore through the post, for pivotally mounting the valve member.

In a certain alternative embodiments, the support member has two projections to provide a "two post" design. In one form, each projection is in the form of a hook-shaped lug which fits around a corresponding pivot portion of the valve member. In another form, each projection is in the form of a lug or post having a bore therein for receiving a respective pivot stub of the valve or tap member.

In any embodiment, the engagement surface of the valve member which engages the flexible tube to pinch it against the support member, may comprise an abrupt edge, or a progressive cam action surface, the latter being preferred.

In a closely related second aspect, the invention provides a pinch valve kit or assembly for use with a drainage bag for selectively pinching closed a flexible outlet tube, comprising a valve member for fitting on a first side of the bag adjacent to the tube, and a support member for fitting on a second side of the bag opposite the valve member, the support member having at least one mounting projection for projecting through a web of the bag to the first side, for pivotally supporting the valve member about a pivot axis generally transverse to the direction of pinch, and the valve member having a handle projection by which it can be manipulated and an engagement surface or edge for pinching the tube against the support member when the valve member is rotated about the pivot axis to a closed position.

In a further closely related aspect, the invention provides a method of assembling a pinch valve to a drainage bag, the method comprising fitting a support plate on one side of the bag adjacent to a flexible outlet tube, such that one or more projections on the support plate pass through a web of the bag to the opposite side of the bag; and fitting a valve member having a handle projection, to the one or more projections on the opposite side of the bag to the support member, such that the valve member is pivotally movable between a closed position in which it pinches the flexible tube against the support member, and an open position in which it does not substantially pinch the outlet tube, the pivot axis being generally transverse to the direction of pinch.

Preferably, the one or more projections are fitted through pre-formed apertures in the web. Preferably, the apertures are dimensioned slightly smaller than at least a part of the projections, such that the projections will form an interlock or an interference fit with the web. This can provide positive retention of the support member relative to the bag, even before the valve member is fitted.

In a further aspect, the invention provides a drainage bag including a flexible outlet tube and a pinch valve for selectively pinching the tube closed, the pinch valve including a pivotable valve member on a first side of the bag and a support member on an opposite side of the bag, wherein the valve member is pivotally supported on the first side of the bag by at least one projection on the support member which projects through an aperture in a web of the bag to the first side.

In a further closely related aspect, the invention provides a pinch valve kit or assembly for use with a drainage bag for selectively pinching closed a flexible outlet tube, comprising a valve member for fitting on a first side of the bag adjacent to the tube, and a support member for fitting on a second side of the bag opposite the valve member, the support member having at least one mounting projection for projecting through a web of the bag to the first side, for pivotally supporting the valve member, and the valve member having a handle by which it can be manipulated, and an engagement surface or edge for pinching the tube against the support member when the valve member is rotated to a closed position.

In a yet further aspect, the invention provides a method of assembling a pinch valve to drainage bag, the method comprising fitting a support plate on one side of the bag adjacent to a flexible outlet tube, such that one or more projections on the support plate pass through a web of the bag to the opposite side of the bag; and fitting a valve member to the one or more projections on the opposite side of the bag to the support member, such that the valve member is pivotally moveable between a closed position in which it pinches the flexible tube against the support member, and an open position in which it does not substantially pinch the outlet tube.

Embodiments of the invention are now described by way of example only, with reference to the accompanying drawings, in which.

Referring to FIGS. 1–5, a drainage bag 10 consists of two sheets of plastics material welded around their periphery to provide a welded seam 12. The seam is enlarged at the bottom of the bag to form two webs 14 on either side of an outlet tube 16 which is sealed between the two sheets of material in the webs 14. The outlet tube 16 is made of a flexible, resiliently deformable material to allow the tube 16 to be pinched closed by a valve assembly 18, in order to seal the bag.

Figure 1:
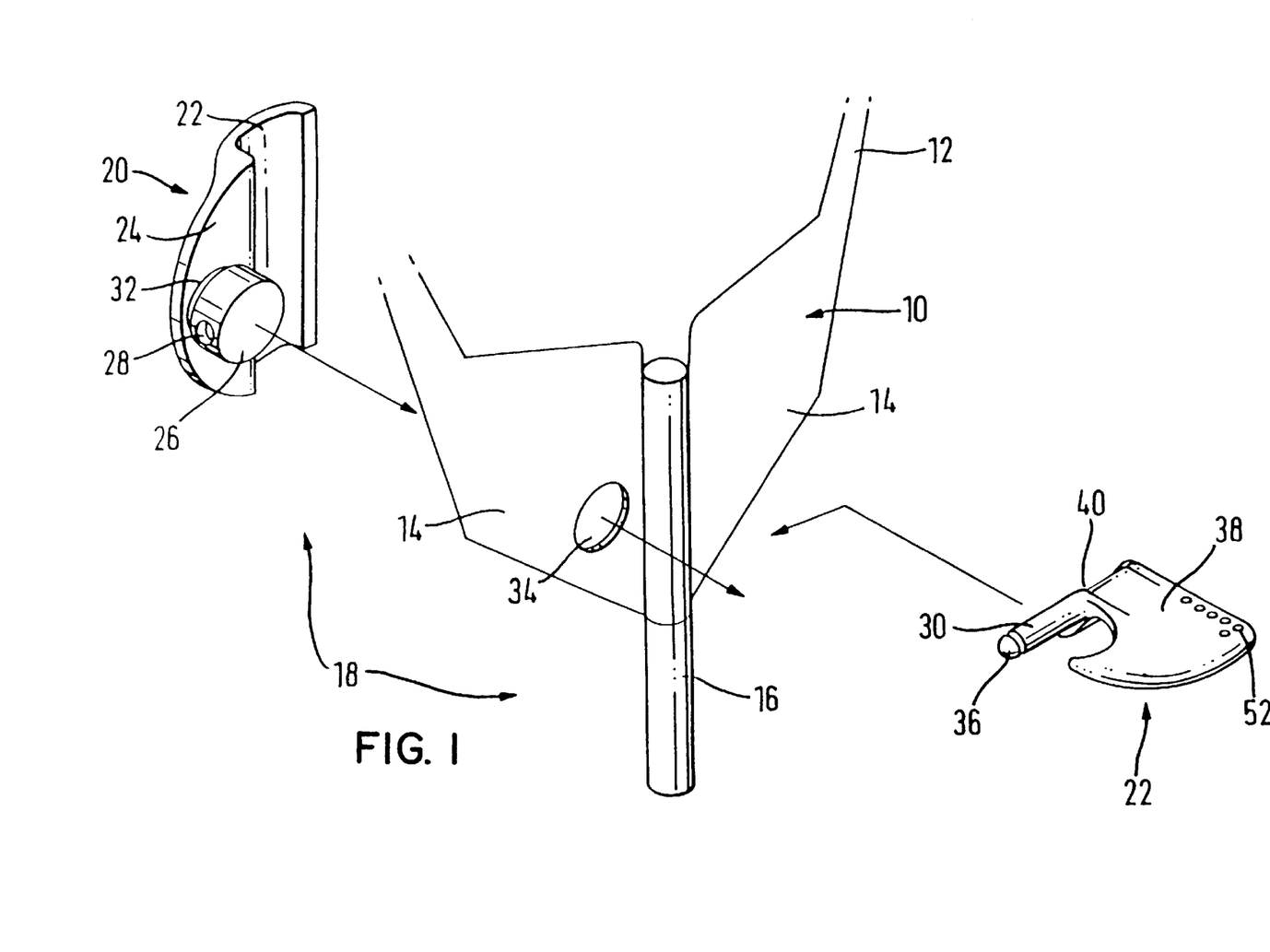
FIG. 1 is an exploded view of a first embodiment of pinch valve.

The valve assembly 18 consists of a rear support member 20 and a pivotally movable valve member 22. The support member 20 consists of a channel-shaped section 22 for fitting around the rear profile of the outlet tube 16, and a lateral extension 24 on one side of the channel section 22. The lateral extension 24 carries a projection in the form of a post 26 with a transverse bore 28 for receiving a pivot pin 30 of the valve member 22. As best seen in FIG. 1, the post 26 is joined to the lateral extension 24 by a short neck 32 which has a slightly smaller diameter than the post 26.

Figure 2:
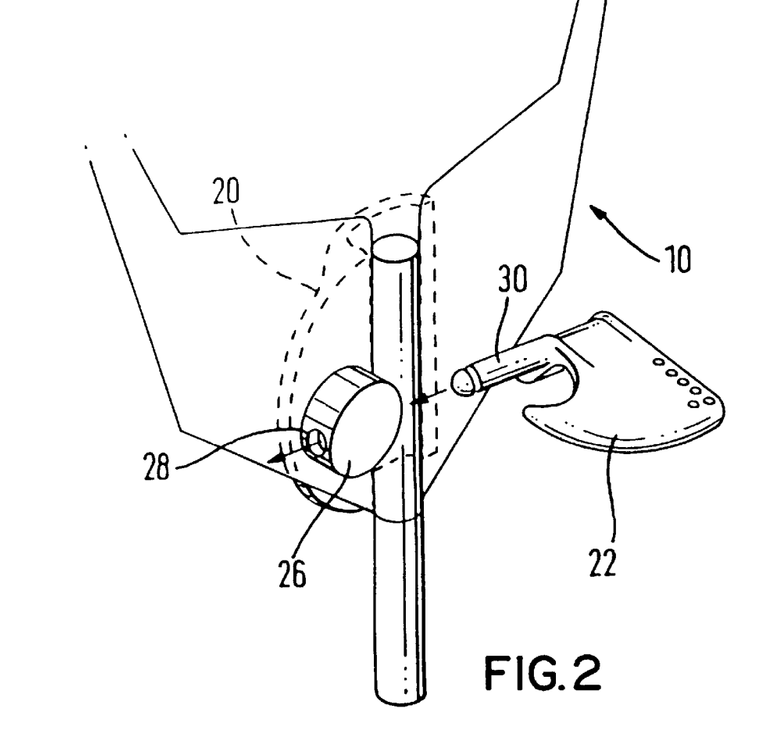
FIG. 2 is a similar view showing the valve in a partially assembled state.

In use, the valve 18 is assembled at the same time as it is fitted to the bag 10. The support member 20 is first fitted to the rear of the bag, and the post 26 is pressed through a pre-formed aperture 34 in the web 14 adjacent to the tube 16. The aperture 34 is dimensioned slightly smaller than the post 26 such that once the post 26 has been forced through the aperture, the web 14 surrounding the aperture 34 will locate in the small recess around the neck 32 behind the post 26. With this arrangement, the support member 22, and hence the whole valve assembly, is positively located and retained against the surface of the web 14.

Next, the pivot pin 30 of the valve member 22 is inserted through the bore 28 of the post now projecting on the front side of the bag. The pivot pin 30 has an enlarged dome head 36 which, once pressed through the bore 28, prevents the pivot pin 30 from accidentally sliding out of the bore.

Figure 3:
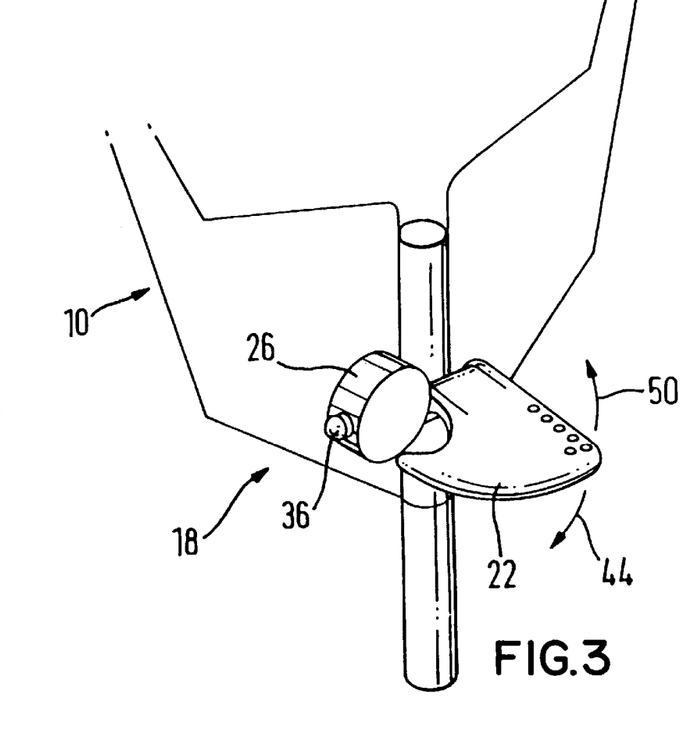
FIG. 3 is a similar perspective view showing the valve in its fully assembled state.
Figure 4:
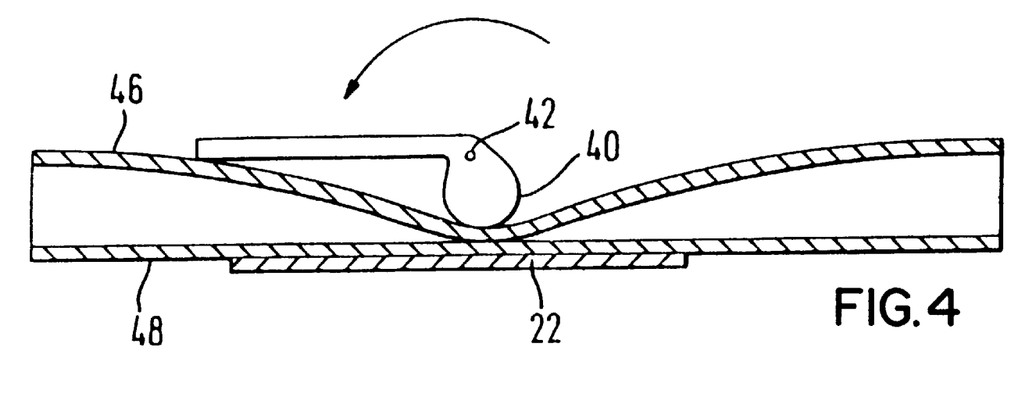
FIGS. 4 and 5 are schematic views illustrating operation of the valve.
Figure 5:
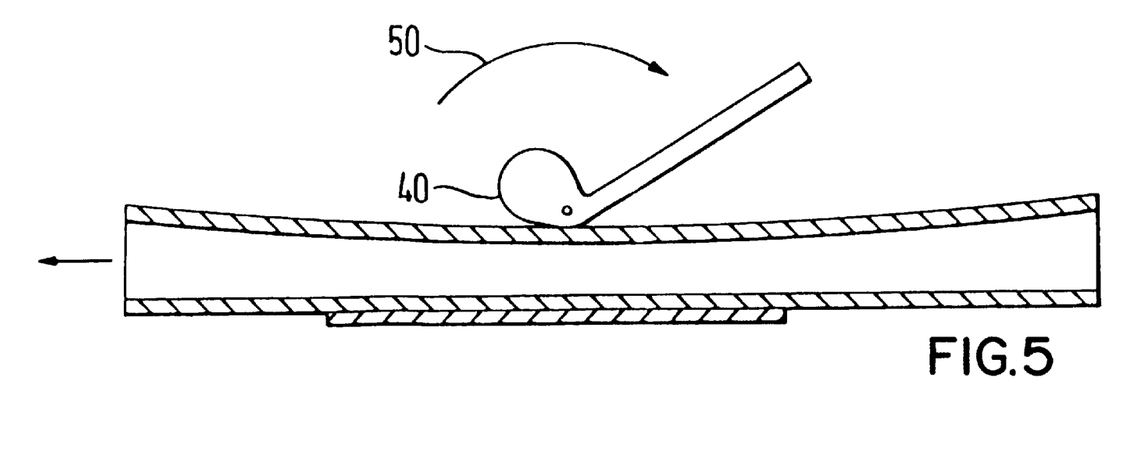

The valve member 22 consists of a handle 38 and a cam surface 40 which are integrally joined to the pivot pin 30. As best seen in FIGS. 4 and 5, the cam surface 40 is part cylindrical, but is offset from the axis 42 of the pivot pin 30 to produce an eccentric action when the valve member is rotated about the pivot axis 42. In normal use of the bag 10, the outlet tube 16 is pinched closed, so that there will be no leakage of the bag contents while the bag is worn by the user. To accomplish this, the handle 38 is moved downwardly in the direction of arrow 44 (FIGS. 3, 4 and 5), which results in the cam surface 40 engaging the front wall 46 of the tube 16, and progressively pressing the front wall 46 towards the rear wall 48 of the tube 16. In the fully closed position of the valve member (FIG. 4), the cam surface 40 firmly pinches the front and rear walls 46 and 48, respectively, of the outlet tube 16 against the base of the channel section 22 of the support member 20. This achieves a fluid-type seal across the whole width of the outlet tube 16.

When the user desires to open the tube 16, for example, to drain the bag contents into a WC, the user moves the handle 38 of the valve member 22 upwardly in the direction of arrow 50. This moves the cam surface 40 progressively away from the wall of the support member 22, thereby un-pinching the tube 16. The tube returns to its natural un-pinched shape by the resilience of the tube material. As best seen in FIG. 5, when the valve member 22 is in its fully open condition, there is very little (or even no) constriction of the tube 16, and this allows the contents of the bag to drain as freely as possible.

The firmness of the pinching engagement ensures that a certain minimum force will be required to move the valve member out of its fully closed position. Additionally, the configuration of the cam surface 40 relative to the pivot axis 42 creates an over-centring effect, to ensure that the valve will not release accidentally, for example, due to movement while the bag is being worn. As can be seen in FIGS. 1 and 3, the handle 38 may be formed with dimples or small protrusions 52 to assist a user's grip.

Figure 6:
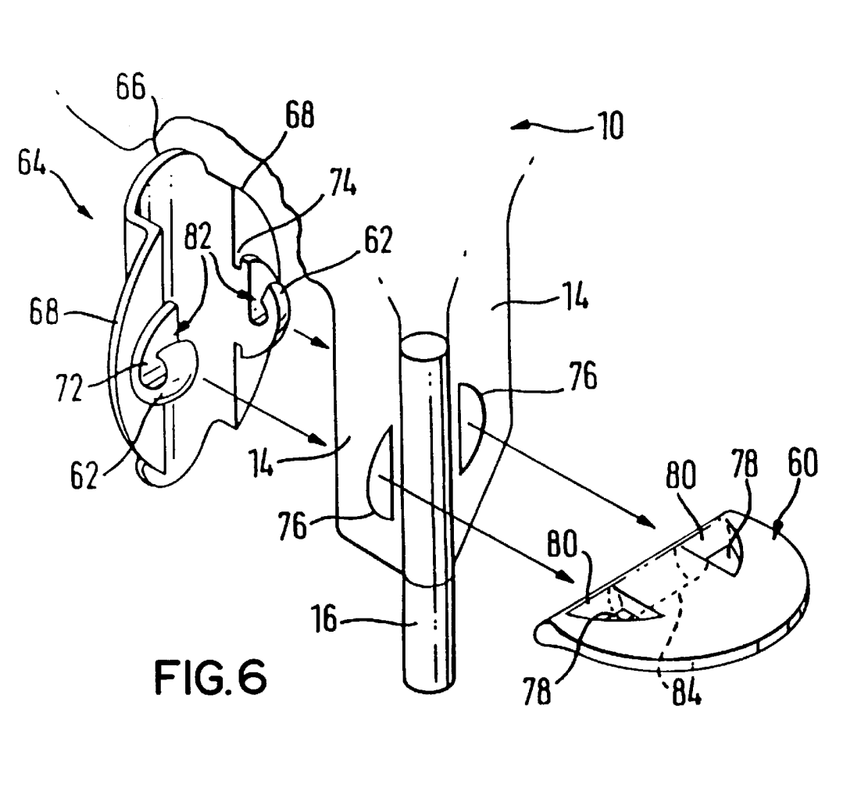
FIG. 6 is an exploded view illustrating assembly of a second embodiment of pinch valve.
Figure 7:
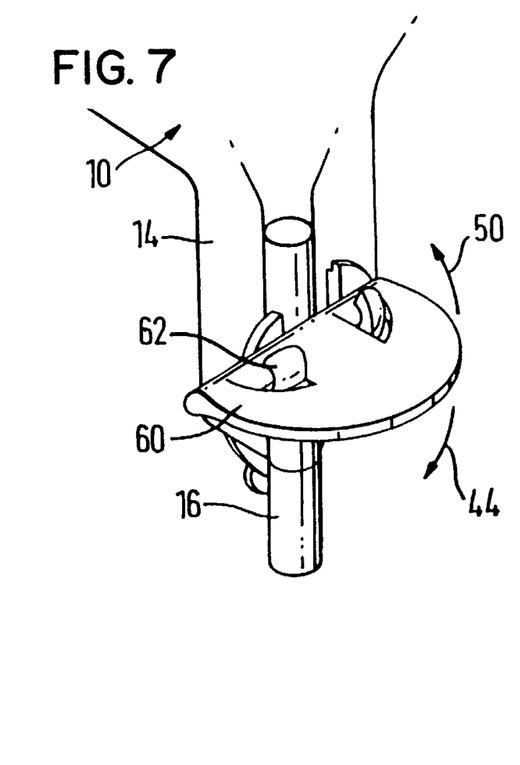
FIG. 7 is a perspective view showing tile second embodiment in its fully assembled state.

FIGS. 6 and 7 illustrate a second embodiment which functions in the same manner as that described above. However, the second embodiment is structurally different in that the valve member 60 is pivotally supported by two projections on the rear support member 64, instead of by a single projection as in the first embodiment. The projections are carried on lateral extensions 68 on either side of the central channel-shaped section 66. Each projection consists of a hook-shaped lug 70 which projects from a semi-circular base 72. In a similar manner to the post 26 and neck 32 of the first embodiment, the semi-circular base 72 is joined to the lateral extension 68 by a short semi-circular neck having slightly smaller dimensions than the base 72.

In use, the support member 64 is fitted from the rear side of the bag 10, and the lugs 70 are inserted through pre-formed semi-circular apertures 76 in the web 14 on either side of the outlet tube 16. The apertures 76 are dimensioned to be slightly smaller than the bases 72 of the lugs 70, such that, once the bases 72 have been forced through the apertures 76, the web material 14 locates behind the bases 72 in the recess around the necks 74. This positively locates and retains the support member 64 on the surface of the web 14 in a similar manner to that described in the first embodiment.

The valve member 60 is generally semi-circular, and includes two apertures 78 behind cylindrical portions 80 on the leading edge of the valve member 60 and in register with the lugs 70. During assembly, once the rear support member has been fitted as described above, the valve member 60 is clipped into the hook-shaped lugs 70 to complete the assembly. The clearance 82 between each lug 70 and its associated base 72 is slightly smaller than the rounded portions 80 of the valve member, but is tapered to allow the valve member to be snapped into position.

The valve member carries a cam surface 84 which functions in exactly the same manner as that illustrated in FIGS. 5 and 6 to pinch the outlet tube 16 when the valve member 60 is pivoted fully downwardly.

Compared to the first embodiment, the second embodiment supports the valve member on either side of the tube 16, and can therefore ensure even more reliable pinching of the outlet tube across its whole width FIGS. 8 to 12 illustrate in isolation the components of a third embodiment, which may be regarded as a combination of the first and second embodiments. The tap member 90 is supported on both sides of the deformable tube (as in the second embodiment), and is pivotally supported by cylindrical bores (as in the first embodiment).

The tap member 90 comprises a handle 92, a compression portion 94, and two pivot stubs 96. The support member 98 comprises a rear channel portion 100, lateral extension portions 102, and support lugs 104. Each lug includes a slightly narrow neck 106 (as in the previous embodiments), is in the shape of a half-dome, and includes a cylindrical bore 108 for receiving a respective one of the pivot stubs 96 of the tap member 90. Each lug 104 also includes a half funnel (or half-Y) shaped entry recess defined by a wall 114 recessed relative to the face 112 of the lug 104, and by an entry ramp 110. The recess acts as a guide for facilitating assembly of the tap member 90 to the rear support member 98.

Figure 8:
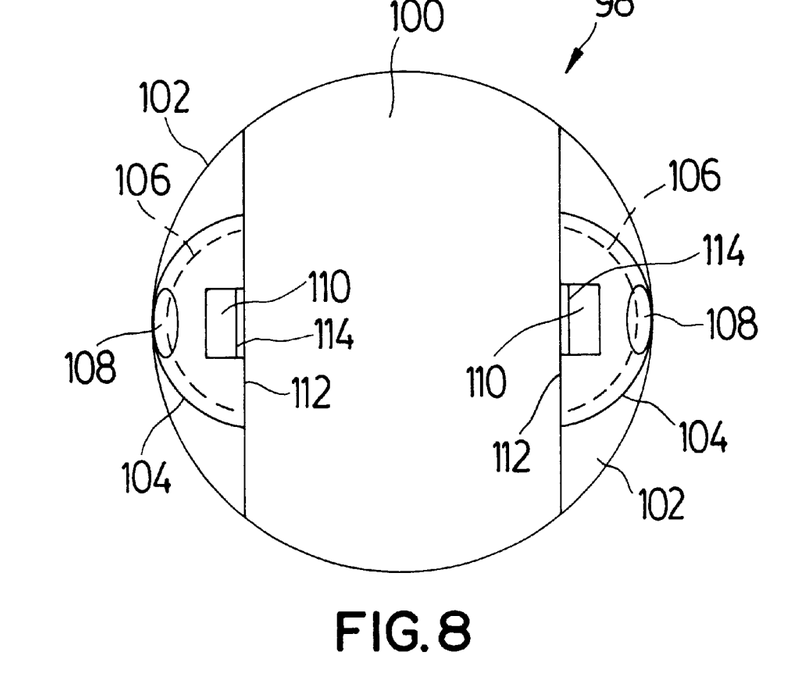
FIG. 8 is a plan view of a rear member of a third embodiment.
Figure 9:
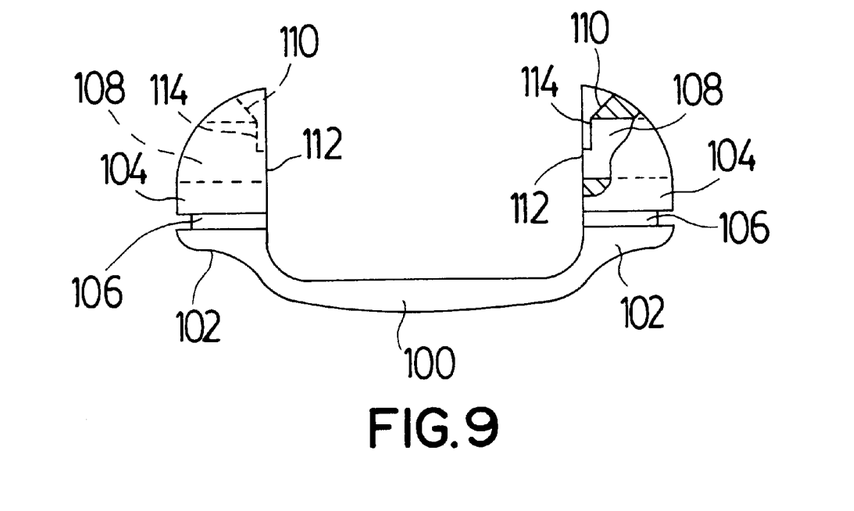
FIG. 9 is a partial cutaway end view of the rear member.
Figure 10:
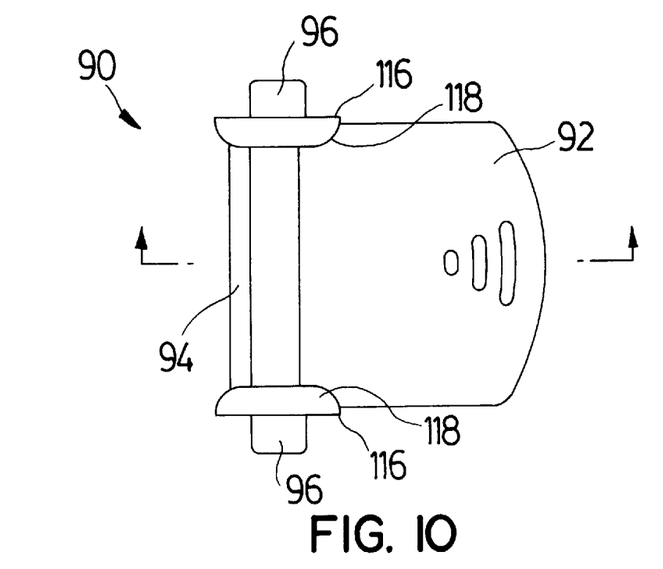
FIG. 10 is a plan view of a tap member of the third embodiment.

In use, to assemble the tap, the lugs 104 of the rear support are first pushed through holes in the wall of the pouch, exactly in the same manner as described in the second embodiment. The tap member 90 is then snapped into place such that the pivot stubs 96 are received in the entry recesses and bear against the ramps 110 to force the lugs 104 outwardly as the tap member 90 is pushed towards the support member 98. It may be easiest to cant the tap member to insert one pivot stub into its respective bore, and to press the tap member until the other pivot stub snaps into its respective bore.

Figure 11:
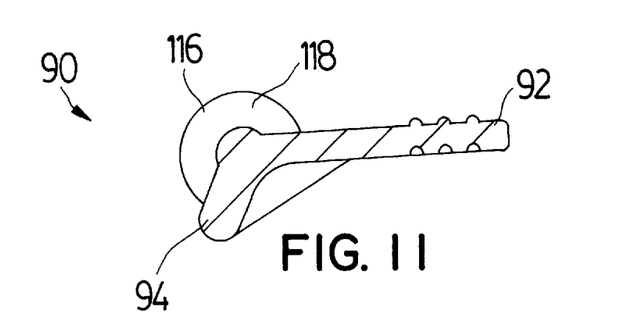
FIG. 11 is a section along the line X—X of FIG. 10.
Figure 12:
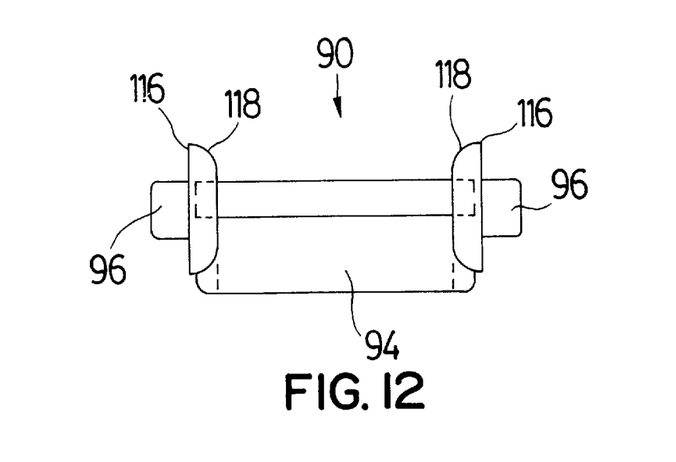
FIG. 12 is an end view of the tip member of FIG. 10

Referring to FIGS. 10, 11 and 12, the tap member includes disc-like abutments 116 from which the pivot stubs 96 project. The abutments 116 bear against the opposing faces 112 of the lugs, and serve to stiffen the tap assembly to prevent it from bending when the tap is in us . It will be appreciated that when the tap is closed, the compression portion 94 of the tap member pressing against the middle of the support member will generate forces tending to bend the channel outwardly at the rear, causing the lugs 104 to lean towards each other. Such distortion (prevented by the abutments) could result in the tap leaking, or being prone to dripping.

The abutments 116 are of about the same height as the dome shaped lugs, and the rear surfaces 118 of the lugs are radiused to provide a smooth, continuous profile where the abutments meet the lugs 104. This can reduce the chances of the ostomate scratching his or her hand on the relatively abrupt edges of the lug around the entry recess, and also reduce the chances of the tap catching on the ostomate's clothing when the pouch is worn.

It will be appreciated that, in other embodiments, if the abutments 116 were omitted, the strength of the tap (i.e. resistance to bending) can be retained by employing a tap member sufficiently wide to bear against the inside faces of the lugs to prevent the lugs from leaning inwardly. However, as explained above, the abutments 116 are preferred to increase customer acceptance.

It will be appreciated that the invention, particularly as illustrated by the preferred embodiments, can provide a valve assembly which is both positively located and positively retained on the bag even when the valve member is in its open position, (i.e. when there is little frictional engagement between the valve member and the outlet tube). Furthermore, the assembling of the valve at the same time as it is fitted to the bag can result in simplified assembly, and more secure fastening.

Although the embodiments have been described with particular reference to ostomy and incontinence bags, the skilled man will appreciate that the invention is not limited exclusively to these fields, but may find wider applications.

I claim:

1. A drainage bag including a flexible outlet tube and a pinch valve for selectively pinching the tube closed, the pinch valve including a pivotal valve member on a first side of the bag and a support member on an opposite side of the bag, wherein the valve member has a handle projection and is pivotally supported on the first side of the bag by at least one projection on the support member which projects through an aperture in a web of the bag to the first side, the valve member being movable by its handle about a pivot axis which is generally transverse to the direction in which the tube is pinched.

2. A bag according to claim 1, wherein the valve member comprises a pivot pin portion for engagement in an opening defined by the projection.

3. A bag according to claim 2, wherein the projection comprises a transverse bore for receiving the pivot pin portion.

4. A bag according to claim 3, wherein the pivot pin portion comprises an enlarged end to obstruct withdrawal of the pivot pin portion from the bore.

5. A bag according to claim 2, wherein the projection is a hook-shaped lug for receiving the pivot pin portion.

6. A bag according to claim 5, wherein the pivot pin portion is a snap fit in the lug.

7. A bag according to claim 1, wherein the aperture has a smaller dimension than a main portion of the projection.

8. A bag according to claim 7 wherein the projection comprises the main projection portion joined to the support member by a neck.

9. A bag according to claim 8, wherein the web material surrounding the aperture interlocks with the projection around the neck.

10. A bag according to claim 1, wherein the valve member comprises an eccentric surface movable into engagement with the tube to pinch the tube.

11. A bag according to claim 1 comprising a plurality of projections for pivotally supporting the valve member.

12. A bag according to claim 1, wherein the bag is a bag for collecting body waste.

13. A pinch valve kit or assembly for use with a drainage bag for selectively pinching closed a flexible outlet tube, comprising a valve member for fitting on a first side of the bag adjacent to the tube, and a support member for fitting on a second side of the bag opposite the valve member, the support member having at least one mounting projection for projecting through a web of the bag to the first side, for pivotally supporting the valve member about a pivot axis generally transverse to the direction of pinch, the valve member having a handle projection by which it can be manipulated and an engagement surface or edge for pinching the tube against the support member when the valve member is rotated about the pivot axis to a closed position.

14. A kit or assembly according to claim 13, wherein the valve member comprises a pivot pin portion for engagement in an opening defined by the projection.

15. A kit or assembly according to claim 14, wherein the projection comprises a transverse bore for receiving the pivot pin portion.

16. A kit or assembly according to claim 14, wherein the projection is a hook-shaped lug for receiving the pivot pin portion.

17. A kit or assembly according to claim 16, wherein the pivot pin portion is a snap fit in the lug.

18. A kit or assembly according to claim 13, wherein the support member comprises a plurality of projections.

19. A method of assembling a pinch valve to a drainage bag, the method comprising fitting a support plate on one side of the bag adjacent to a flexible outlet tube, such that one or more projections on the support plate pass through a web of the bag to the opposite side of the bag; and fitting a valve member having a handle projection, to the one or more projections on the opposite side of the bag to the support member, such that the valve member is pivotally movable between a closed position in which it pinches the flexible tube against the support member, and an open position in which it does not substantially pinch the outlet tube, the pivot axis being generally transverse to the direction of pinch.

20. A method according to claim 19, wherein the projection is inserted through a corresponding pre-formed aperture.

21. A method according to claim 20, wherein the aperture is smaller than a predetermined portion of the projection, and the method comprises forcing the predetermined portion of the projection through the aperture such that the material of the web locates behind the predetermined portion of the projection.

22. A drainage bag including a flexible outlet tube and a pinch valve for selectively pinching the tube closed, the pinch valve including a pivotal valve member on a first side of the bag and a support member on an opposite side of the bag, wherein the valve member is pivotally supported on the first side of the bag by at least one projection on the support member which projects through an aperture in a web of the bag to the first side.

23. A pinch valve kit or assembly for use with a drainage bag for selectively pinching closed a flexible outlet tube, comprising a valve member for fitting on a first side of the bag adjacent to the tube, and a support member for fitting on a second side of the bag opposite the valve member, the support member having at least one mounting projection for projecting through a web of the bag to the first side, for pivotally supporting the valve member, the valve member having a handle by which it can be manipulated, and an engagement surface or edge for pinching the tube against the support member when the valve member is rotated to a closed position.

24. A method of assembling a pinch valve to a drainage bag, the method comprising fitting a support plate on one side of the bag adjacent to a flexible outlet tube, such that one or more projections on the support plate pass through a web of the bag to the opposite side of the bag; and fitting a valve member to the one or more projections on the opposite side of the bag to the support member, such that the valve member is pivotally moveable between a closed position in which it pinches the flexible tube against the support member, and an open position in which it does not substantially pinch the outlet tube.

* * * * *